(12) United States Patent
Termaten

(10) Patent No.: US 6,221,072 B1
(45) Date of Patent: Apr. 24, 2001

(54) DEVICE FOR FIXING BONE SECTIONS RELATIVE TO EACH OTHER

(76) Inventor: Gerrit Johannes Termaten, Nieuwe Maanderbuurtweg 808, 6717 AZ Ede (NL)

( * ) Notice: Subject to any disclaimer, the term of this patent is extended or adjusted under 35 U.S.C. 154(b) by 0 days.

(21) Appl. No.: 09/288,297

(22) Filed: Apr. 8, 1999

(51) Int. Cl.[7] ..................................................... A61F 5/04
(52) U.S. Cl. .............................. 606/54; 606/57; 606/59
(58) Field of Search ................................ 606/54, 53, 59; 128/92; 403/90

(56) References Cited

U.S. PATENT DOCUMENTS

| | | | |
|---|---|---|---|
| 2,238,870 | * | 4/1941 | Haynes ..................... 128/92 |
| 4,620,533 | * | 11/1986 | Mears ..................... 128/92 Z |
| 5,098,432 | * | 3/1992 | Wagenknecht ............ 606/54 |
| 5,746,741 | * | 5/1998 | Kraus et al. ............... 606/54 |
| 5,769,851 | | 6/1998 | Veith ......................... 606/57 |
| 5,921,985 | * | 7/1999 | Ross, Jr. et al. ............ 606/59 |

FOREIGN PATENT DOCUMENTS

| | | |
|---|---|---|
| 424 292 | 4/1991 | (EP) . |
| 699 419 | 3/1996 | (EP) . |
| 2 665 353 | 2/1992 | (FR) . |
| 2 024 632 | 1/1980 | (GB) . |
| 95/10240 | 4/1995 | (WO) . |

\* cited by examiner

Primary Examiner—Michael Buiz
Assistant Examiner—Anthony S. King
(74) Attorney, Agent, or Firm—Foley & Lardner

(57) ABSTRACT

A device for fixing bone sections relative to each other, comprises a support bar for lateral application along the bone sections to be fixed. The support bar includes at least two sliding pieces slidable and fixable on the support bar and each being provided with a spherical part. A bone pin locking block is provided with a cup-shaped portion which is fittingly received on the spherical portion of the sliding piece, in such a way that the bone pin locking block, after having been pivoted into the desired position, can be fixed onto the sliding piece. Each of the two opposite sides of a bone pin locking block is provided with a protruding portion for fastening pivotably adjustable clamping beds cooperating with clamping plates fixable thereon and thus clamping the bone pins in their positions.

6 Claims, 4 Drawing Sheets

DEVICE FOR FIXING BONE SECTIONS RELATIVE TO EACH OTHER

BACKGROUND OF INVENTION

1. Field of the Invention

The invention relates to a device for fixing bone sections relative to each other, comprising a support bar for lateral application along the bone sections to be fixed, said support bar having at least two bone pin looking blocks being slidable across and securable on said support bar, each of two opposite sides of said blocks being provided with a protruding portion for fastening pivotably adjustable clamping beds, in which bone pins can be pressed against said clamping beds by means of clamping plates to be secured on the clamping beds, said clamping beds and clamping plates being engaging planes for the bone pins and both clamping beds can be secured relative to each other in such a way that their engaging planes for the bone pins enclose a sharp angle.

2. Description of Related Art

In professional circles, such a device is called an "external fixator" and is applied to assist in the healing of bone fractures. A device of the type described above is known from WO 95/10240.

With this device, after applying the pins in the bone sections and securing them to the support bar through the bone pin locking blocks, the bone sections can be pressed towards each other or be spaced apart across a certain distance. This occurs by sliding the bone pin locking blocks across the support bar.

A difficulty is that after mounting the device, the bone sections can only perform the movement described above and that other movements of the bone sections relative to each other are hardly possible.

BRIEF SUMMARY OF INVENTION

The object of the invention is to remove this difficulty and to that end provides for, that a sliding piece fixable on the support bar is mounted between each bone pin locking block and the support bar, and said sliding piece is provided with a spherical portion, whereas the bone pin locking block is provided with a cup-shaped portion which is matingly received on the spherical portion of said sliding piece, in such a way, that the bone pin locking block, after having been pivoted into the desired position, can be fixed on the sliding piece.

In this way, it is achieved that the two bone pin locking blocks have much more freedom of movement relative to each other before they are fixed onto the sliding piece and thus through the latter onto the support bar. Therefore, in certain cases, the bone sections connected with it can be brought into a more suitable position relative to each other as a result of which the healing process can be accelerated.

It is possible to provide a cavity in the bone pin locking block, in which the spherical portion of the sliding piece can be received in such a way that it will contact a stop surface. The cavity can then be closed by an externally threaded ring to be screwed into the block.

However, it is important that the dimensions of the sliding piece be kept as small as possible and that securing the bone pin locking block onto the sliding piece is as simple as possible. To that end, according to the invention it will be provided for, that each bone pin locking block is divided in two parts according to a plane going through the axis of the support bar in the centre position of said block, the parts at one side being pivotably connected to each other and at the opposite side being able to be pulled towards each other by a bolt in such a way that the parts can enclose the spherical portion of the sliding piece and can be clamped thereon.

Thus, a simple construction and an easy connection between the bone pin locking block and the sliding piece is achieved. The block can also be clamped onto the sliding piece in a simple way and thus be fixed relative to the support bar through said sliding piece.

With the known device mentioned above, the contact planes for the bone pins are partially constituted by two parallel grooves made in a clamping plate.

According to a further development of the invention, each clamping bed can now be provided with at least two clamping plates which can be pressed against the clamping bed in any angular position by means of one bolt, each of which being provided with contact planes for one bone pin.

In this way it is achieved, that the two bone pins to be clamped onto a clamping bed need not be parallel but can enclose an angle. Thus, two bone pins, together with the bone, can form a triangle as a result of which a more rigid structure is achieved than when the bone pins are parallel. Furthermore, the locations where the bone pins are secured in a bone can be situated wider apart.

In order to be able to press the bone sections connected by means of a fixator continuously against each other, one of the sliding pieces can be brought under an adjustable compressive load by means of a length-adjustable compression spring.

Now in certain cases it is desirable that after a certain time, the sliding pieces are moved slightly towards each other or moved slightly apart. The latter is the case e.g. when a bone must be extended and the bone sections growing towards each other must be moved slightly apart repeatedly.

In order to be able to realize this in a simple way, according to the invention, one can employ an adjustment member consisting of a bush being slidable on the support bar and comprising means for clamping it onto at a certain position on the support bar, said bush being provided with an external thread on which a set screw can be screwed, said screw being rotatably connected to a sliding piece, said sliding piece being connected to a blade spring extending towards a portion of the circumferential surface of the set screw, said surface being provided with a number of flat sides mounted circumferentially.

By rotating the set screw in one or the other direction the sliding piece can be moved in the desired direction. By the presence of the blade spring and the flat sides on the set screw it is known across which distance a sliding piece is moved when the blade spring, on rotating the set screw, will get from its one flat side onto its next flat side.

BRIEF DESCRIPTION OF DRAWING

The invention is further explained by way of an embodiment, shown in the drawing, in which.

DETAILED DESCRIPTION OF THE PREFERRED EMBODIMENTS

Figure 1:
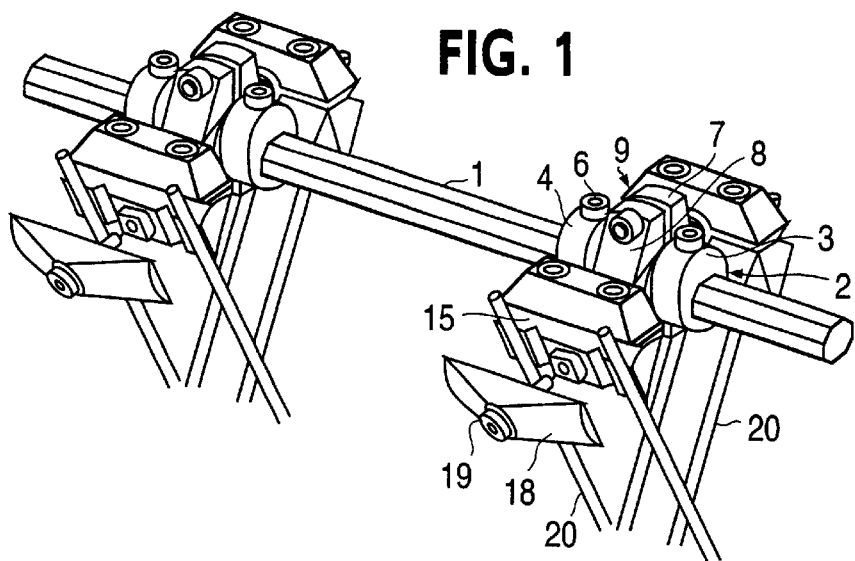
FIG. 1 is a perspective view of a device according to the invention, in which some parts are illustrated separately.

The device illustrated in the drawing comprises the support bar 1 across which sliding pieces 2 are slidable. A sliding piece consists of a spherical portion 3 situated between two disc portions 4 having threaded holes 5 for receiving a screw 6. The sliding piece 2 can be clamped onto the support bar 1 by the screw 6.

The spherical portion 3 supports a bone pin locking block 9 consisting of two parts 7 and 8. To that end, the parts 7 and 8 each have a cup-shaped portion 10 and are each provided with a slot 11 in which a link 12 can be fittingly received. The link 12 is secured in the parts 7 and 8 by means of a pin not further indicated. In this way, the parts 7 and 8 are pivotably connected. By bores situated at the other side of the parts 7 and 8, a bolt 13 can be mounted to be able to pull the parts 7 and 8 towards each other and clamp them onto the spherical portion 3.

As known from WO 95/10240, the parts 7 and 8 are provided with a spherical portion 14 on which a bone pin clamping bed 15 has been pivotable mounted. The clamping bed 15 can be clamped onto the portion 14 by means of clamping brackets 16 and screws 17. A clamping bed 15 cooperates with a clamping plate 18 forced against the clamping bed by a bolt 19 in order to clamp bone pins 20 between said clamping bed and the clamping plate.

The bone pins 20 can be mounted in a bone in the known way and further handling of the device is likewise known. With the embodiment according to FIG. 1, the bone sections not illustrated are properly positioned relative to each other by means of the pins 20, the clamping plates 18, the bolts 19, the clamping beds 15 and the bone pin locking blocks 9, whereupon the various parts are fixed relative to each other.

Figure 2:
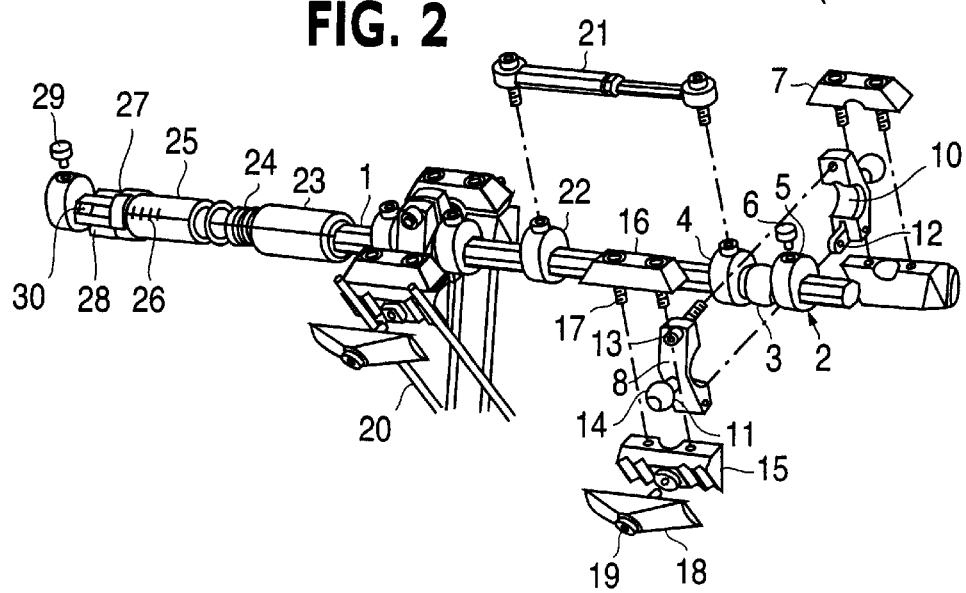
FIG. 2 is a view corresponding to FIG. 1, in which a number of parts have been added.

In the embodiment according to FIG. 2, an intermediate rod 21 comprising parts that can be threaded together has been provided. One part is connected to a disc 4 of a sliding piece 2 and the other part to a disc 22 clamped onto the support bar 1. By rotating the one part of the intermediate rod 21 the sliding piece 2 can be pushed away from the disc 22 or be pulled towards it. The spacing between the bone sections can then be adjusted or be gradually reduced to the desired degree.

FIG. 2 shows the possibility to bring one bone pin locking block 9 under a certain load. To that end, a pressure bush 23 contacting the sliding piece 2 and internally comprising a spring 24 being received at the other side by a set screw bush 25 partially located in the pressure bush 23 is employed. On moving the set screw bush 25 within the pressure bush 23 the force exerted by the spring 24 will change. The exerted force can be read from a scale 26 on the set screw bush 25. Moving the set screw bush 25 within the pressure bush 23 can take place in that the set screw bush 25 contacts a nut 27 being rotatable on a threaded sliding part 28 which can be secured on the support bar 1 by means of a set screw 29. Possibly, the spring 24 can contact the nut 27 directly. The sliding part 28 can be provided with a scale 30 so that it is possible to read the distance across which the set screw bush 25 is moved.

Figure 2A:
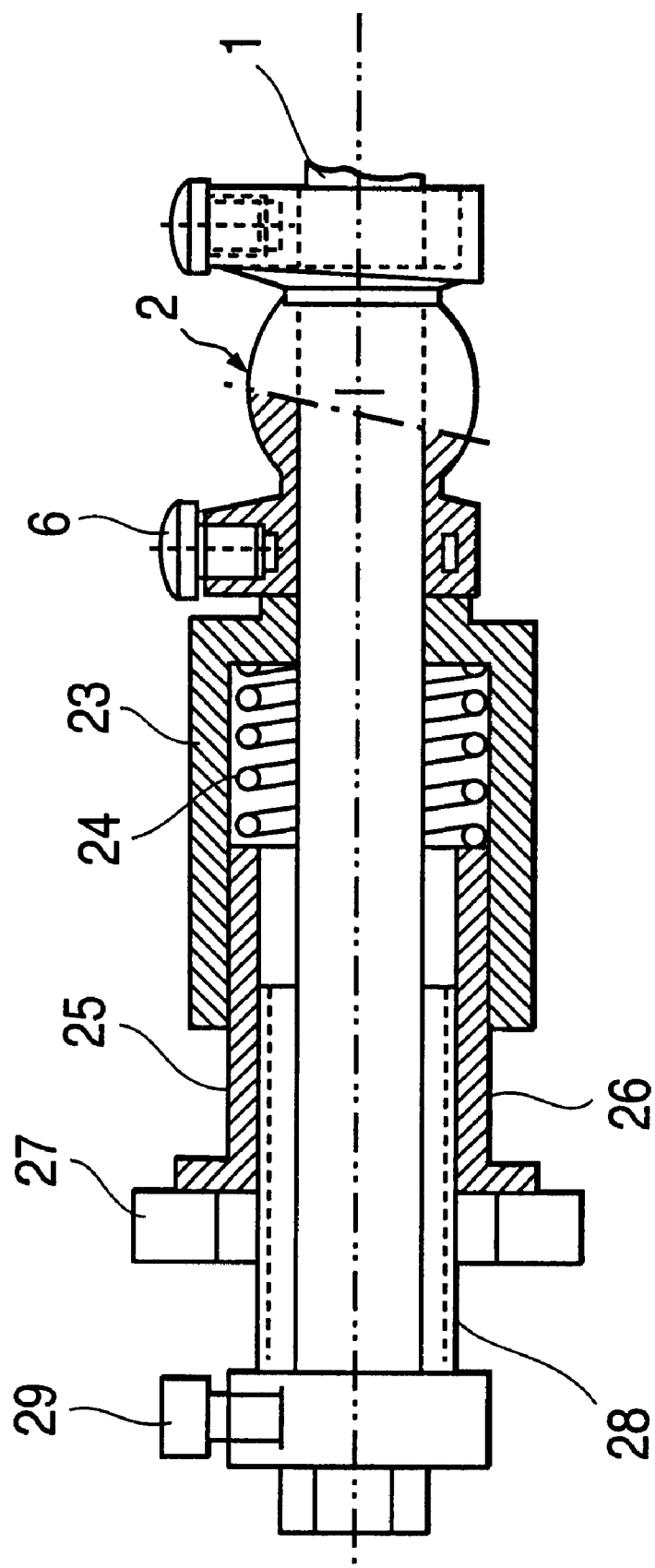

When one wants to press the pieces of bone against each other, the parts in FIG. 2 that are indicated by the reference numbers 23–30 are used. Further explanation of this aspect of the present invention is discussed with reference to FIG. 2A, which shows a side view partly in longitudinal section, of the related parts of FIG. 2.

On the support bar 1 the pressure bush 23 is mounted, being movable in the longitudinal direction. It engages the sliding piece 2, the screws 6 of which are loosened. The bush 23 is biased by a spring 24 engaging the set screw bush 25 being movable in the longitudinal direction on the sliding part 28 which is fixed onto bar 1 by the clamping screw 29. The part 28 is provided with a screw thread on which the nut 27 can be rotated. The bush 25 can be pressed against the spring 24 by nut 27, which in turn will press the bush 23 against the sliding piece 2 being provided with the bone pins 20. In this way the piece 2 is pressed towards the other piece 2 which can be fixedly clamped onto the bar 1. The force exerted on the piece 2 by the bush 23 is related to the distance over which the bush 25 is moved into the bush 23. By measuring this distance, the force can be determined.

Figure 3:
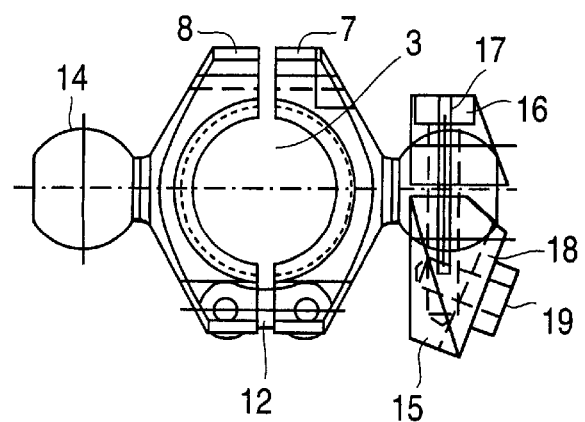
FIG. 3 is a view, on an enlarged scale, of some parts illustrated in the FIGS. 1 and 2.

FIG. 3 shows the spherical portion 3 with the parts 7 and 8 mounted thereon and provided with the spherical portions 14 with some further parts on one of them.

Figure 4:
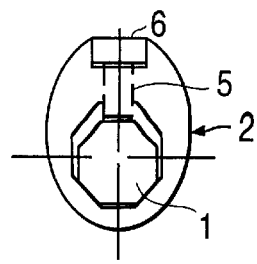
FIG. 4 is a cross-section across a support bar and a 15 part secured on it.

FIG. 4 shows the support bar 1 and a sliding piece 2 in cross-section. By such an embodiment, the sliding piece can be clamped firmly onto the support bar 1.

In the FIGS. 1 and 2, the pins 20 to be mounted in a bone, which are clamped onto one single clamping bed 15, extend in parallel.

However, it is also possible to have the pins extending obliquely apart to the bone section concerned, from a clamping bed 15. It has turned out, that then the pins are able to accommodate more forces and due to that can be designed thinner. Obviously, this facilitates bringing the pins into the bone.

It will be obvious, that the clamping beds 15 must be designed for that, in that the grooves made therein will have to enclose a sharp angle. However, the clamping beds 15 can easily be replaced by other ones, e.g. when a bone section has only a small length and thus the pins in the bone must be situated close to each other.

Figure 5:
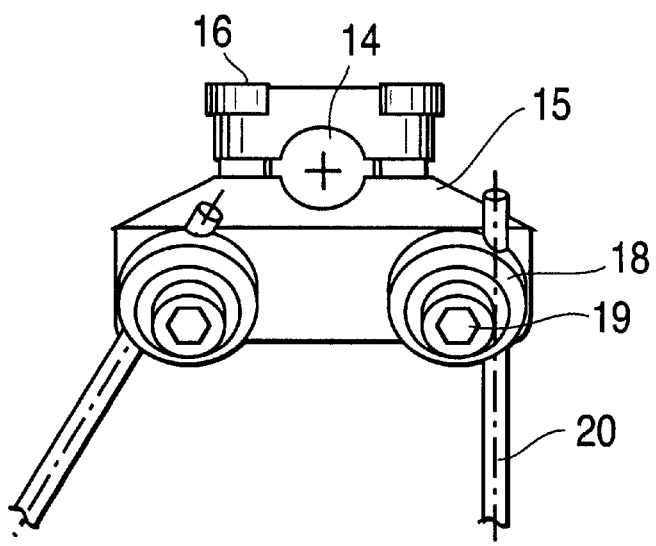
FIG. 5 is a view of a bone pin locking block with a clamping bed and clamping plates mounted on said clamping bed.

FIG. 5 shows the possibility of realizing a flat clamping bed 15 and providing it with two separate clamping plates 18 which contain the grooves in which the bone pins 20 are received in order to be clamped. Each of the clamping plates 18 is clamped by a bolt 19. The angle enclosed by the bone pins 20 can then be chosen freely.

Figure 6:
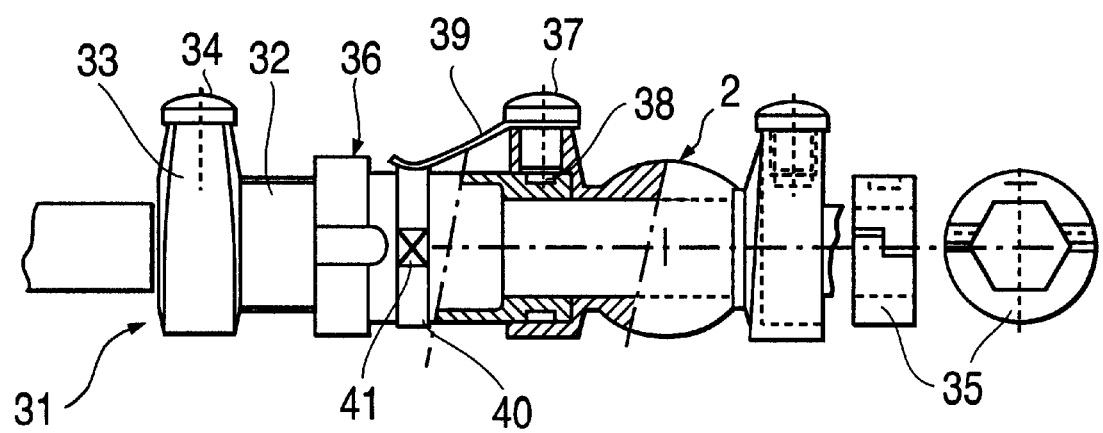
FIG. 6 is a side view and partial cross-section of an adjustment member for a sliding piece, said member being mounted on a support bar.

FIG. 6 further shown an adjustment member 31 comprising a bush 32 which is slidable on the support bar 1 and can be clamped on a certain location of the support bar 1 by means of a disc 33 connected to it and a clamping screw 34 mounted therein. Here, possibly a ring 35 comprising two parts and incorporated in the disc, as illustrated in side view and end view at the right in FIG. 6, can be employed separately from the other parts. Then, the force exerted by the clamping screw 34 is more evenly transmitted to the support bar 1. When desired, the sliding piece 2 can also be secured on the support bar 1 by means of such a ring.

The bush 32 is provided with an external thread on which a set screw 36 can be screwed, which is rotatably connected to a sliding piece 2, in that it accommodates a screw 37 located in a groove 38 exending circumferentially in said set screw 36.

Figure 6A:
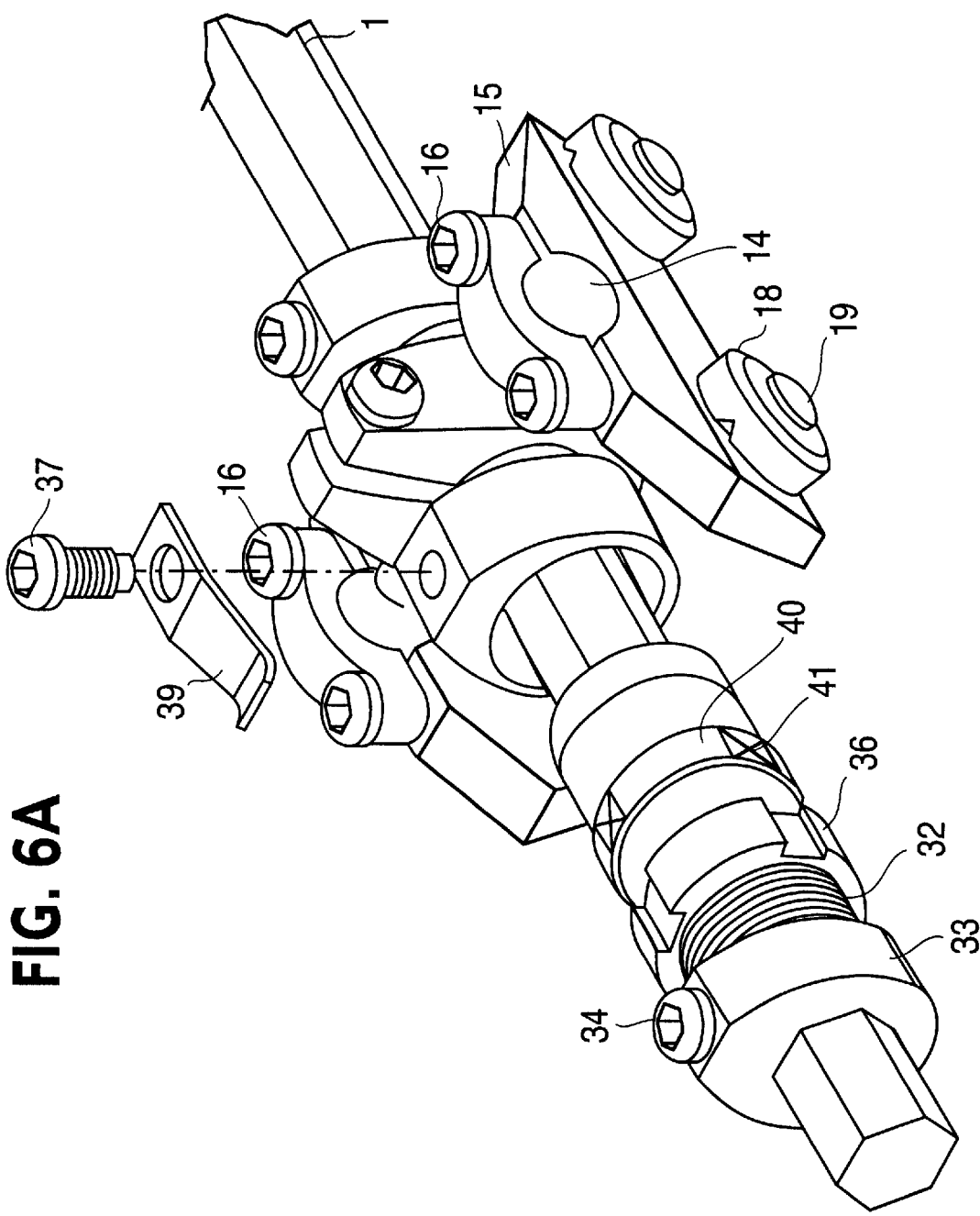

Here, the sliding piece 2 is connected to a blade spring 39 extending towards a portion 40 of the circumferential surface of the set screw 36, said portion 40 being provided with a number of flat sides 41 located in circumferential direction. By the presence of the blade spring 39 and the flat sides 41 on the set screw 36, the distance across which a sliding piece 2 is moved when the blade spring, on rotation of the set screw, gets from the flat side 41 onto the next flat side, is indicated. Further structural detail of the adjustment member is also shown in FIG. 6A.

It will be obvious, that only some possible embodiments of a device according to the invention have been illustrated in the drawing and described above and that many modifications can be made without leaving the inventive idea, as it is indicated in the claims.

What is claimed is:

1. A device for fixing bone sections relative to each other, comprising:

a support bar for lateral application along a bone section to be fixed;

at least two bone pin locking blocks being slidable across and securable on said support bar;

a protruding portion provided on each of two opposite sides of said blocks for fastening pivotably adjustable clamping beds, in which a bone pin can be pressed against said clamping beds by clamping plates to be secured on the clamping beds, said clamping plates to be secured on said clamping beds, said clamping beds and clamping plates being engaging planes for the bone pins and both clamping beds can be secured relative to each other such that their engaging planes for the bone pins enclose an angle less than 180 degrees relative to each other; and a sliding piece fixable on the support bar mounted between each bone pin locking block and the support bar, said sliding piece is provided with a spherical portion, the bone pin locking block being provided with a cup-shaped portion which is fittingly received on the spherical portion of said sliding piece such that the bone pin locking block after having been pivoted into the desired position, can be fixed onto the sliding piece.

2. The device according to claim 1, wherein the clamping beds are executable such that the bone pins extend obliquely apart from said clamping beds.

3. The device according to claim 1, wherein each bone pin locking block is divided in two parts according to a plane going through the axis of the support bar in the center position of said block, the two parts being pivotably connected to each other by a link at one side and the two parts being able to be pulled towards each other by a bolt at the opposite side such that the parts can enclose the spherical potion of the sliding piece and can be clamped thereon.

4. The device according to claim 3, further comprising:

at least two clamping plates provided with each clamping bed which can be pressed against the clamping bed in any angular position relative to a plane of said clamping bed by one bolt, each of said clamping plates being provided with contact planes for a bone pin.

5. The device according to claim 1, further comprising:

a length-adjustable compression spring contactable with a sliding piece for bringing said sliding piece under an adjustable compressive load.

6. The device according to claim 1, further comprising:

an adjustment member that includes
      a bush being slidable on the support bar, and
      clamping means for clamping said bush onto the support bar at a certain position thereof, said bush being provided with an external thread on which a set screw can be screwed, a blade spring being connected to the sliding piece, said spring extending towards a portion of the circumferential surface of the set screw, said surface being provided with a number of flat sides mounted circumferentially.

* * * * *